United States Patent [19]

Schmidhauser

[11] Patent Number: 5,480,959
[45] Date of Patent: Jan. 2, 1996

[54] SUBSTANTIALLY PURE BISPHENOLS AND POLYMERS COMPRISING BISPHENOLS

[75] Inventor: John C. Schmidhauser, Schenectady, N.Y.

[73] Assignee: General Electric Company, Schenectady, N.Y.

[21] Appl. No.: 226,099

[22] Filed: Apr. 11, 1994

Related U.S. Application Data

[63] Continuation of Ser. No. 61,948, May 17, 1993, abandoned.

[51] Int. Cl.$^6$ ................................ C08G 64/00
[52] U.S. Cl. ............... 528/198; 528/196; 528/199; 528/200; 558/265
[58] Field of Search ............... 568/722, 723, 568/727, 730; 558/265; 528/198, 196, 199, 200

[56] References Cited

U.S. PATENT DOCUMENTS

| | | |
|---|---|---|
| 2,596,235 | 5/1952 | Geiger . |
| 2,811,564 | 10/1957 | Bader . |
| 3,378,525 | 4/1968 | Sellers . |
| 3,380,965 | 4/1968 | Matzner ................. 360/47 |

OTHER PUBLICATIONS

Tetrahedron Letters, vol. 30, No. 12, 1989, Andersen et al., "Hjydrallmanol A", pp. 1487–1490.
Journal of Polymer Science, Polymer Chemistry Edition, vol. 3, 1965, Strenstrom et al., "Gas Permeability of Three Isomeric Polyhydroxyethers", pp. 3843–3851.

Primary Examiner—Paul J. Killos
Assistant Examiner—Samuel Barts
Attorney, Agent, or Firm—Edward A. Squillante, Jr.; William H. Pittman

[57] ABSTRACT

Bisphenols are prepared from cyclic monoterpene precursors and high glass transition temperature polymers are prepared from bisphenols. More particularly, substantially pure 4-[1-[3-(4-hydroxyphenyl)-4-methylcyclohexyl]-1-methylethyl] phenol and 4,4'-[1-methyl-4-methylethyl]-1,3-cyclohexandiyl] bisphenol are isolated and high glass transition temperature bisphenol polycarbonates are prepared.

5 Claims, No Drawings

5,480,959

SUBSTANTIALLY PURE BISPHENOLS AND POLYMERS COMPRISING BISPHENOLS

This application is a continuation of application Ser. No. 08/061,948, filed May 17, 1993 now abandoned.

FIELD OF THE INVENTION

This invention relates to new compositions of matter, and more particularly to novel substantially pure bisphenols prepared from cyclic monoterpene precursors as well as high glass transition temperature polycarbonates comprising bisphenols. Further, a method is disclosed for isolating the above-mentioned substantially pure bisphenols.

BACKGROUND OF THE INVENTION

Polycarbonates are a well known class of high impact resistant thermoplastic resins characterized by optical clarity, high ductility as well as other advantageous properties. They are frequently employed as lenses and windows as a result of their transparency. Bisphenol A (BPA) polycarbonate is the predominant commercially available resin of this type. It is derived from 2,2-bis(4-hydroxyphenyl)propane and ordinarily has a glass transition temperature of about 150° C.

It is of increasing interest to prepare polycarbonates which, while retaining the ductility of BPA, have higher glass transition temperatures and are therefore more resistant to softening when heated.

Polycarbonates possessing increased glass transition temperatures are very desirable, for instance, in the automotive and aircraft industries. Particularly, they may be used in the preparation of automotive headlamp lenses which are becoming smaller in size and characterized by closer proximity of the lenses to the heat-generating light source.

The present invention is based on the discovery and method of isolation of substantially pure bisphenols; in particular, 4-[1-[3-(4-hydroxyphenyl)-4-methylcyclohexyl]-1-methylethyl]phenol (hereinafter referred to as BPT-1) and 4,4'-[1-methyl-4-(1-methylethyl)-1,3-cyclohexandiyl] bisphenol (hereinafter referred to as BPT-2) and homologs thereof and homopolycarbonates and copolycarbonates prepared from bisphenols. Substantially pure is defined as at least about 95% pure. The resulting homopolycarbonates possess increased glass transition temperatures on the order of about 198° C. when employing BPT-1 and about 249° C. when employing BPT-2. Moreover, copolycarbonates of BPT-1 and BPA as well as BPT-2 and BPA may be prepared which are also expected to display increased glass transition temperatures.

DESCRIPTION OF THE PRIOR ART

Accordingly, attempts have been made to prepare polycarbonates that possess high glass transition temperatures in addition to clarity, high ductility and superior impact strengths. In commonly assigned, copending applications, Ser. Nos. 07/989,309 and 07/989,310, it is disclosed that polycarbonates prepared from 1,3-bis(4-hydroxyphenyl)-1,3-dialkylcyclohexanes and bis[4'-4(hydroxyphenyl)-phenyl] alkanes, respectively, display glass transition temperatures on the order of about 10° C. to about 45° C. higher when compared to conventionally used polymers. Moreover, in commonly assigned, copending application Ser. No. 07/989,316, it is disclosed that polycarbonates prepared from heterocyclic bis(4-hydroxyphenyl)cycloalkanes possess glass transition temperatures on the order of about 35° C. to about 84° C. higher when compared to typical resins.

Other investigators have focused their attention on the preparation of bisphenols. For example, *Chemical Abstracts:* Volume 65, columns 7315 and 7316 (1966) and 59271w, volume 68 (1968) and 191233q, volume 101 (1984) and *Journal of Polymer Science: Part A*, volume 3, pp. 3843–3851 (1965) all disclose bisphenols in which the phenol groups are attached to an aliphatic ring. However, the instant invention is patentably distinguishable from the above-mentioned references since, among other reasons, the former isolates substantially pure BPT-1 and BPT-2 as well as homologs thereof. Moreover, the instant invention incorporates BPT-1 and BPT-2, as well as their homologs, into novel high glass transition temperature polycarbonates. Such polycarbonates can include novel high glass transition homopolycarbonates of BPT-1 and BPT-2 and copolycarbonates of BPT-1 and BPA, BPT-2 and BPA, BPT-1 and BPT-2 and BPT-1, BPT-2 and BPA.

SUMMARY OF THE INVENTION

The present invention therefore is the discovery and method of isolation of substantially pure bisphenois prepared from cyclic monoterpenes and the preparation of novel, ductile, high glass transition temperature thermoplastic aromatic polycarbonates prepared from bisphenols. More particularly, the substantially pure bisphenol substituted polycarbonates comprise structures of the formulae

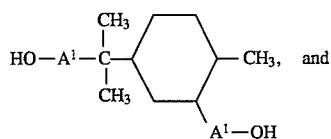

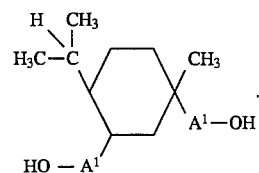

In each of said units independently, each $A^1$ is independently a divalent substituted or unsubstituted aromatic radical. However, it is most preferred that the bisphenols are 4-[1-[3-(4-hydroxyphenyl)-4-methylcyclohexyl]-1-methylethyl]-phenol (BPT-1) and 4,4'-[1-methyl-4-(1-methylethyl)-1,3-cyclohexandiyl] bisphenol (BPT-2) and represented by the formulae

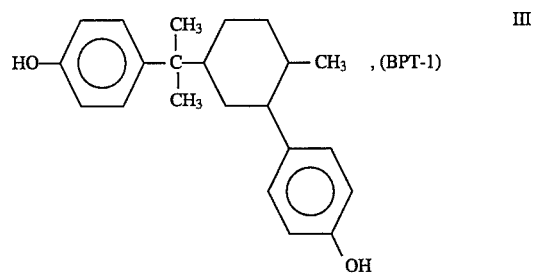

and

-continued

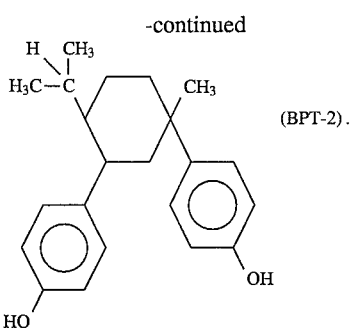

(BPT-2). IV

Furthermore, the structures depicted hereinabove are not limited to any sterioisomeric (cis or trans) arrangement. The cis- and trans-isomers may be separated by fractional crystallization or by flash column chromatography, typically using a mixture of ethyl acetate and hexane as the eluents.

DETAILED DESCRIPTION OF THE PREFERRED EMBODIMENTS

The bisphenol substituted polycarbonates described above may also comprise structural units of the formulae

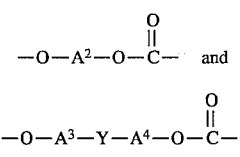

whereby VI is a preferred subgenus of V.

$A^2$ is a divalent substituted or unsubstituted aliphatic, alicyclic or aromatic radical and each of $A^3$ and $A^4$ is a monocyclic divalent aromatic radical and Y is a bridging radical in which one to four atoms separate $A^3$ from $A^4$. The free valence bonds in formula VI are usually in the meta or para positions of $A^3$ and $A^4$ in relation to Y.

The $A^3$ and $A^4$ values may be unsubstituted phenylene or substituted derivatives thereof, illustrative substituents (one or more) being alkyl, alkenyl, halo (especially chloro and/or bromo), nitro, alkoxy and the like. Unsubstituted phenylene radicals are preferred. Both $A^3$ and $A^4$ are preferably p-phenylene, although both may be o- or m-phenylene or one o-or m-phenylene and the other p-phenylene.

The bridging radical, Y, is one in which one or two atoms, preferably one, separate $A^3$ from $A^4$. It is most often a hydrocarbon radical and particularly a saturated radical such as methylene, cyclohexylmethylene, 2-[2.2.1]-bicycloheptylmethylene, ethylene, isopropylidene, neopentylidene, cyclohexylidene, cyclopentadecylidene, cyclododecylidene or adamantylidene, especially a gem-alkylene (alkylidene) radical. Also included, however, are unsaturated radicals and radicals which contain atoms other than carbon and hydrogen; for example, 2,2-dichloroethylidene, carbonyl, phthalidylidene, oxy, thio, sulfoxy and sulfone. For reasons of availability and particular suitability for the purposes of this invention, the preferred units of formula VI are 2,2-bis(4-phenylene)propane carbonate units, which are derived from bisphenol A and in which Y is isopropylidene and $A^2$ and $A^3$ are each p-phenylene.

Further, it is within the scope of the invention to include units of the formula

HO—$A^2$—OH,   (VII)

which is the source of structural units of formula V above;

$A^2$ is as previously defined.

Illustrative non-limiting examples of VII include:

2,2-bis(4-hydroxyphenyl)-propane (bisphenol A);

2,2-bis(3,5-dibromo-4-hydroxyphenyl)propane;

2,2-bis(3,5-dimethyl-4-hydroxyphenyl)propane;

1,1-bis(4-hydroxyphenyl)cyclohexane;

1,1-bis(3,5-dimethyl-4-hydroxyphenyl)cyclohexane;

1,1-bis(4-hydroxyphenyl)decane;

1,4-bis(4-hydroxyphenyl)propane;

1,1-bis(4-hydroxyphenyl)cyclododecane;

1,1-bis(3,5-dimethyl-4-hydroxyphenyl)cyclododecane;

4,4-dihydroxydiphenyl ether;

4,4-thiodiphenol;

4,4-dihydroxy-3,3-dichlorodiphenyl ether; and 4,4-dihydroxy-3,3-dihydroxydiphenyl ether.

Other useful dihydroxyaromatic compounds which are also suitable for use in the preparation of the above copolycarbonates are disclosed in U.S. Pat. Nos. 2,999,835; 3,028,365; 3,334,154 and 4,131,575, all of which are incorporated herein by reference. The preferred bisphenol is 2,2-bis(4-hydroxyphenyl)propane (bisphenol A).

The copolycarbonates of the instant invention may also contain units corresponding to the dihydroxy compounds disclosed by name or formula (generic or specific) in U.S. Pat. No. 4,217,438, the disclosure of which is incorporated herein by reference. Such copolycarbonates typically comprise about 25–75% by number of substantially pure bisphenol units (cis- or trans-isomers or both) with the balance being alternative units such as those depicted by formulae V and VI.

The preferred substantially pure bisphenols of the instant invention may be converted to polycarbonates by reacting with a carbonate source such as phosgene or dimethyl carbonate using conventional techniques. These include melt polymerization, interfacial polymerization and interfacial conversion bischloroformate followed by polymerization. Chain termination agents such as phenol may also be employed.

Said polycarbonates comprise structural units of the formulae

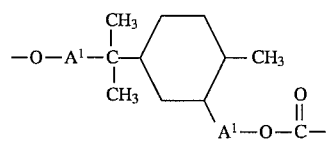

and

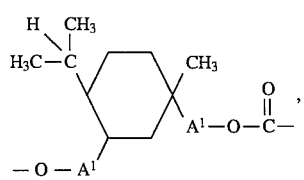

wherein $A^1$ is as previously defined.

However, it is most preferred that the polycarbonates comprise structural units of the formulae

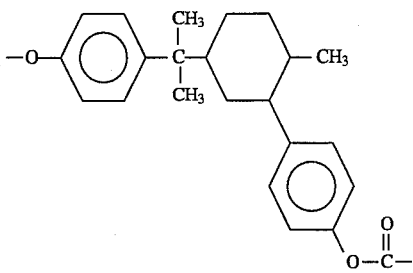

and

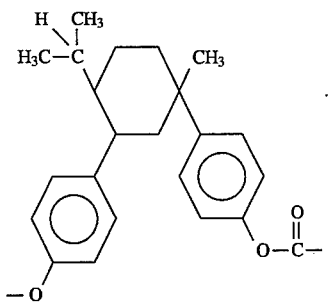

The bisphenols of the instant invention may be prepared by reacting phenols with a variety of cyclic monoterpenes under acidic (Bronsted or Lewis) conditions. For instance, reacting γ-terpinene with seven equivalents of phenol and an acidic ion-exchange resin at 100° C. yields a crude mixture containing about 41% BPT-1 and about 16% BPT-2 as well as additional phenol containing compounds. A similar crude mixture may also be obtained with some degree of difference when employing other cyclic terpenes such as alpha terpinene, 2- and 3-carene, α-terpinol, α-pinene, sabinene, limonene and dipentene as well as mixtures thereof. In addition to acidic ion exchange resins, a number of acid catalysts may be used (both Bronsted and Lewis) including boron trifluoride etherate, aluminum trichloride and phosphoric acid. Moreover, reaction temperatures may vary resulting in no substantial effect on product formation.

Methods for isolating I and II from the above-described crude mixtures are not known. The instant invention therefore provides for a novel purification/isolation process. As a result of the process, I may be isolated from II whereby both I and II are at least about 95% pure.

The method of isolating I from II, and particularly III from IV, entails heating the above-described crude mixture to a temperature of about 50°–60° C. followed by the addition of solvents such as chloroform in an amount equal to about one-half the volume of the crude mixture. Subsequently, the above obtained crude mixture/chloroform solution is stirred and cooled to about room temperature producing a thick oily mixture in which a tan crystalline solid deposits therefrom. The crystalline solid is recovered therefrom by filtration and a BPT-2 containing flitrate is obtained. Via $H^1$ and $^{13}C$ NMR analysis, as well as physical property analysis (i.e., melting point analysis), it was determined that, after the first filtration, the crystalline solid was about 90% BPT-1. The BPT-1 solid above was then recrystallized and filtered from solvents such as chloroform, chlorobenzene or a mixture thereof resulting in the formation of at least about 95% pure BPT-1 solid and a second BPT-2 containing flitrate. Further, the BPT-2 containing flitrates were subjected to evaporation to produce a tan glassy solid which was recrystallized in isopropyl alcohol. The requisite amount of isopropyl alcohol is about one-half to 100 percent of the volume of the tan glassy solid recovered. Finally, the isopropyl alcohol and BPT-2 mixture was heated in a vacuum oven above the boiling point of isopropyl alcohol for approximately 3 days. The resulting product was at least about 95% pure BPT-2.

The following examples are provided to further facilitate the understanding of the invention and they are not intended to limit the instant invention. All substantially pure bisphenols produced were confirmed by proton and carbon 13 nuclear magnetic resonance spectroscopy as well as X-ray crystallographic techniques.

EXAMPLE 1

Synthesis and Purification/Isolation of Substantially Pure BPT-1 and BPT-2

A solution of phenol (2000g, 21.2 mole), gamma terpinine (424.5g, 3.11 mole) and acidic ion exchange resin (200.0g, Amberlyst 31, sulfonated polystyrene-divinylbenzene gel with 4.94 meq. H+/gram resin) was heated to 95°–110° C. for 20 hours. Analysis via HPLC indicated a crude product composition of about 41% BPT-1 and 16% BPT-2 as well as additional phenol by-products. The crude mixture was filtered through a glass funnel to remove ion exchange resin beads. The filtrate was distilled at a reduced pressure of 1 mmHg at 70° C. in order to remove phenol and produce a distillation residue. Chloroform (600 ml) was added to the residue which was at a temperature of 50° C. The residue and chloroform mixture was cooled to ambient temperature over a period of 10 hours in order to produce crude tan crystalline BPT-1 solid. The crude BPT-1 solid was recovered from the chloroform mixture via filtration whereby a BPT-2 containing filtrate was retained. The crude BPT-1 solid was recrystallized from chloroform resulting in white crystals of substantially pure BPT-1 (290g) as well as additional BPT-2 filtrate. The above filtrates were concentrated in a vacuum oven in which a second white solid (BPT-2) deposited therefrom. The second white solid was recovered via filtration; it was recrystallized from isopropyl alcohol producing substantially pure BPT-2 (29g).

EXAMPLE 2

Polycarbonate of BPT-1

A solution was prepared containing 11.0g (0.0339 mole) BPT-1,100 ml $CH_2Cl_2$, 85 ml water, 1.4 ml of 5% triethylamine/$CH_2Cl_2$ solution and 2.25 ml of 5% phenol/$CH_2Cl_2$ solution. While maintaining the pH between 10.5 and 11.5 via 10% (aq) NaOH addition, phosgene gas was introduced for 20 minutes at a flow rate of about 0.35 g/min. A polymer containing system was produced. The system was purged with nitrogen gas for about 15 minutes and washed two times with 3% HCL solution and four times with water. The washed solution was dried over $MgSO_4$ and poured into MeOH to induce precipitation. The precipitate was subsequently redissolved in $CH_2Cl_2$. The resulting solution ws subjected to acetonitrile to again induce precipitation. The precipitate was redissolved in $CH_2Cl_2$. 10.7g of the desired polycarbonate powder was finally reprecipitated by again adding MeOH.

EXAMPLE 3

Polycarbonate of BPT-2

The identical procedure of Example 2 was performed using the following reagents: 5.50g (0.0169 mole) BPT-2, 50 ml CH$_2$Cl$_2$, 45 ml water, 1.0 ml of 5% triethylamine/CH$_2$Cl$_2$ solution, 1.1 ml of 5% phenol/CH$_2$Cl$_2$ solution as well as 0.30 g/min of phosgene for 13 minutes. The polycarbonate produced (4.90 g) was isolated as a white powder.

EXAMPLE 4

35:65 BPT-I:BPA Copolycarbonate

The identical procedure of Example 2 was performed using the following reagents: 561.6 g (1.73 mole) BPT-1, 734 g (3.22 mole) BPA, 10.01 CH$_2$C$_2$, 7.01 water, 9.0 ml (1.25 mole %) triethylamine, 16.25g (3.5 mole %) phenol and 25.7 g/min of phosgene for 30 minutes. The copolycarbonate produced was isolated as 1000 g of white powder.

The data in the table which follows has been compiled to demonstrate that polycarbonates containing BPT-1 and BPT-2 possess superior glass transition temperatures (Tg).

| Entry | Polycarbonate | Tg °C. | Mw* | Mw/Mn* |
|---|---|---|---|---|
| 1 | BPT-1 Homopolycarbonate | 198.0 | 76,700 | 3.34 |
| 2 | BPT-2 Homopolycarbonate | 249.0 | 89,500 | 1.57 |
| 3 | BPT-1/BPA Copolycarbonate** | 171.0 | 56,500 | 1.69 |

*Values measured relative to polystyrene standards by GPC.
**35/65 percent by mole of BPT-L/BPA It is also noted that Entry 3 has a notched Izod impact strength of about 3.8 ftlb/in wherein conventional polycarbonates, which contain 35 mole percent of a typical high-Tg comonomer, display notched Izod impact strengths of less than 1.0 ftlb/in.

What is claimed is:

1. A bisphenol polycarbonate polymer consisting of aromatic polycarbonate units and comprising at least one of the structural units of the formulae

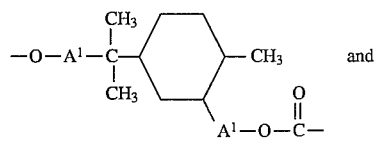

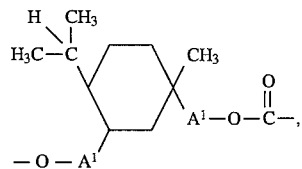

wherein each A$^1$ is independently a divalent substituted or unsubstituted aromatic radical.

2. A bisphenol polycarbonate in accordance with claim 1 wherein said polycarbonate is a homopolycarbonate.

3. A bisphenol polycarbonate in accordance with claim 1 wherein said polycarbonate is a copolycarbonate.

4. A bisphenol polycarbonate in accordance with claim 3 wherein said copolycarbonate also comprises structural units of the formula

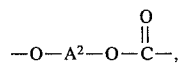

wherein A$^2$ is a divalent substituted or unsubstituted aliphatic, alicyclic or aromatic radical.

5. A bisphenol copolycarbonate in accordance with claim 3 wherein said copolycarbonate also comprises structural units of the formula

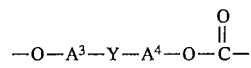

and A$^3$ and A$^4$ are each independently a monocyclic divalent aromatic radical wherein Y is a bridging radical.

* * * * *

UNITED STATES PATENT AND TRADEMARK OFFICE
CERTIFICATE OF CORRECTION

PATENT NO. : 5,480,959

DATED : January 2, 1996

INVENTOR(S) : John C. Schmidhauser

It is certified that error appears in the above-identified patent and that said Letters Patent is hereby corrected as shown below:

On the title page: Item [56] Reference Cited:
"Hjydrallmanol A" should read --Hydrallmanol A--; at column 2, under the SUMMARY OF THE INVENTION, line 26, "bisphenois" should read --bisphenols--; at column 6, under EXAMPLE 2, line 60, "HCL" should read --HCl--.

Signed and Sealed this

Twenty-eighth Day of May, 1996

Attest:

BRUCE LEHMAN

*Attesting Officer*     *Commissioner of Patents and Trademarks*